United States Patent [19]

Kidawara et al.

[11] Patent Number: 4,862,258

[45] Date of Patent: Aug. 29, 1989

[54] MULTIPLE CHARACTERISTIC ENDOSCOPE LIGHT SOURCE FOR FRAME SEQUENTIAL COLOR IMAGING, MOSAIC COLOR IMAGING AND FIBER IMAGE GUIDE SCOPES

[75] Inventors: Atsushi Kidawara, Tachikawa; Toshiaki Nishikori, Sagamihara; Masahide Kanno; Hisao Yabe, both of Hachioji; Shinichi Katoh; Yuji Ikuno, both of Oume; Takeaki Nakamura, Hino, all of Japan

[73] Assignee: Olympus Optical Co., Ltd., Tokyo, Japan

[21] Appl. No.: 188,775

[22] Filed: Apr. 29, 1988

[30] Foreign Application Priority Data

May 13, 1987 [JP] Japan ................................. 62-116403
May 13, 1987 [JP] Japan ................................. 62-116404

[51] Int. Cl.⁴ ......................... H04N 7/18; A61B 1/06
[52] U.S. Cl. .......................................... 358/98; 128/6
[58] Field of Search ............................. 358/98, 92, 93; 128/4–6

[56] References Cited

U.S. PATENT DOCUMENTS 4,621,284 11/1986 Nishioka et al. ................... 128/6 X
4,667,229 5/1987 Cooper et al. .......................... 358/98
4,710,807 12/1987 Chikama .............................. 358/98

FOREIGN PATENT DOCUMENTS 60-76888 5/1985 Japan .
60-243625 12/1985 Japan .
61-82731 4/1986 Japan .

Primary Examiner—James J. Groody
Assistant Examiner—Victor R. Kostak
Attorney, Agent, or Firm—Armstrong, Nikaido, Marmelstein, Kubovcik & Murray

[57] ABSTRACT

The endoscope light source apparatus of this invention has a light source for emitting a white color light as an illuminating light and a connecting part connectable with the light guide of the endoscope. Reflecting members are movably provided in the light path connecting the light source and the connecting part, and switch the light path between a light path through which the illuminating light adapted to an endoscope provided with a frame sequential type imaging device can be made to enter a filter which can sequentially transmit it and a light path which can avoid the filter.

7 Claims, 10 Drawing Sheets

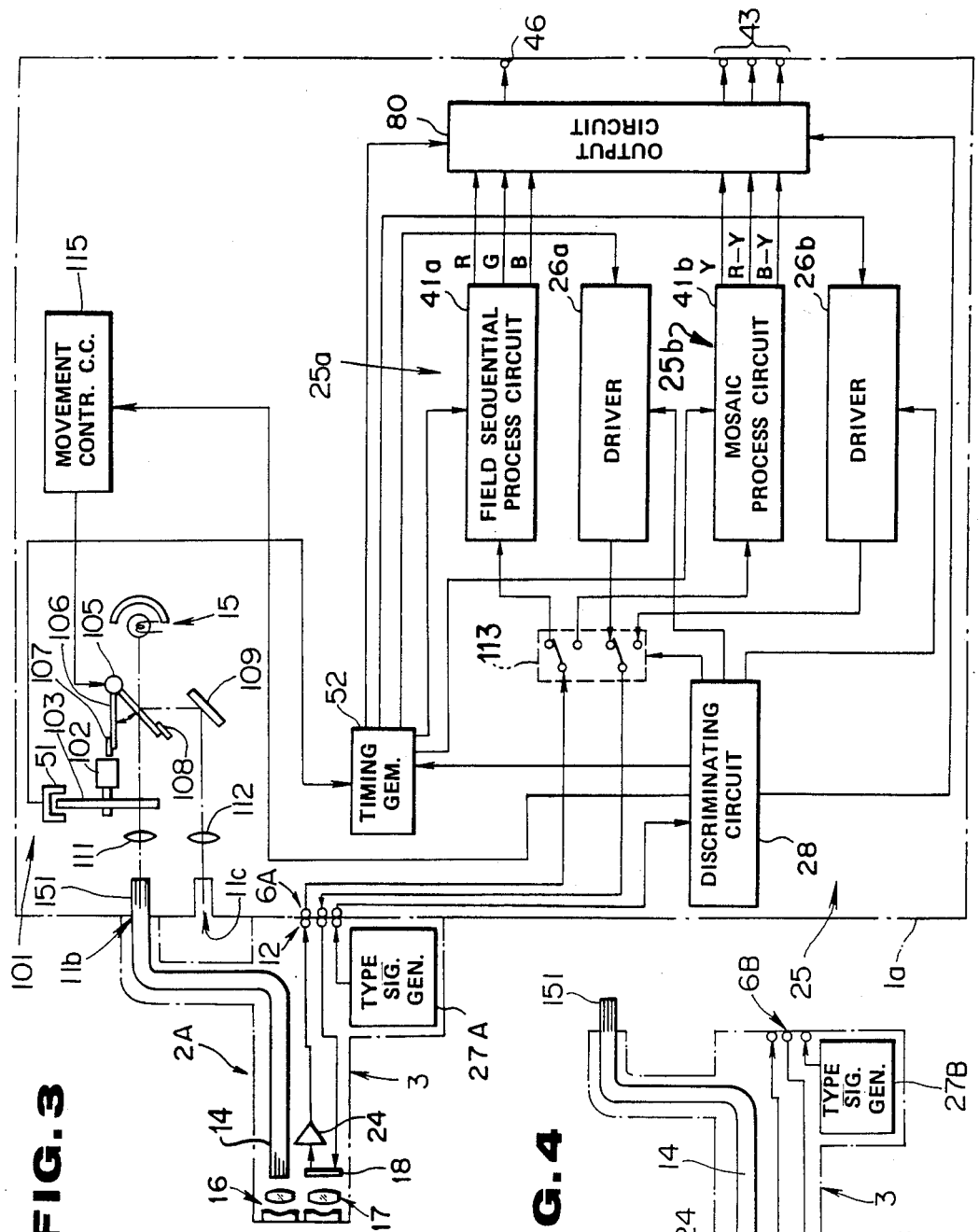

MULTIPLE CHARACTERISTIC ENDOSCOPE LIGHT SOURCE FOR FRAME SEQUENTIAL COLOR IMAGING, MOSAIC COLOR IMAGING AND FIBER IMAGE GUIDE SCOPES

FIELD OF THE INVENTION

This invention relates to an light source apparatus which can feed an illuminating light adapted to a scope provided with a frame sequential type imaging means, a scope provided with a color mosaic type imaging means and a fiber image guide scope.

BACKGROUND OF THE INVENTION

Recently, there is extensively used an endoscope (called a scope or fiber scope) whereby organs within a body cavity can be observed by inserting a fine diameter insertable part into the body cavity or, as required, various curing treatments can be made by using a treating tool inserted through a treating tool channel.

Also, an electronic scope wherein such solid state imaging device as a charge coupled device (CDD) is used is variously suggested. This electronic scope has such advantages that the resolution is higher than in a fiber scope, it is easy to record and reproduce picture images and such picture image treatments as the magnification of picture images and the comparison of two picture images area are easy.

Among the systems of imaging color picture images of the above mentioned electronic scope, there are such frame sequential type wherein the illuminating light is sequentially switched to R (red), G (green) and B (blue) as as shown, for example, in the gazette of a Japanese patent application laid open No. 82731/1986 and such color mosaic type (called also a simultaneous type) wherein a filter array in which color filters transmitting respectively such color lights as of R, G and B are arranged in the form of a mosaic is provided on the front surface of a solid state imaging device as is shown, for example, in the gazette of a Japanese patent application laid open No. 76888/1985. The frame sequential type has an advantage that pixels can be made fewer than in the color mosaic type. On the other hand, the color mosaic type has an advantage that no color displacement is produced for a quickly moving object to be imaged.

There are many kinds of the above mentioned electronic scope depending on the intended use. For example, an insertable part of an outside diameter of about 10 mm. is used for an upper or lower digestive organ. On the other hand, an insertable part of an outside diameter less than about 5 mm. is usually required, for example, for bronchia. Thus, it is physically and functionally unreasonable to use the same kind of imaging device and the same kind of imaging system for various electronic scopes in which the outside diameter of the insertable part varies in a wide range. That is to say, for example, in order to realize an electronic scope for bronchia (fine diameter), it is necessary to use an imaging device of few pixels.

Thus, in case the pixels are few, in order to prevent the reduction of the resolution, the frame sequential type color imaging system wherein an object is illuminated in a frame sequential system with lights of respective wavelengths, for example, of R, G and B and frame sequential images are made under this illumination and are combined to color-display the object image is more advantageous than the color mosaic type imaging system wherein color mosaic filters are used.

On the other hand, it is advantageous for the improvement of the picture quality to make the imaging system a color mosaic type by increasing pixels for the outside diameter of about 10 mm.

Now, the above mentioned fiber scope or electronic scope is used generally as connected to a light source apparatus feeding illuminating lights adapted to the respective scopes.

The illuminating method is different among the above mentioned fiber scope, frame sequential type electronic scope and color mosaic type electronic scope. That is to say, a white color light is required for the fiber scope and color mosaic type electronic scope. A light which is sequentially switched to respective color tones of such frame sequential type as of R, G and B is required for the frame sequential type electronic scope. However, conventional light source apparatus can output only an illuminating light corresponding to either one of the frame sequential type electronic scope and color mosaic type electronic scope or fiber scope. Therefore, the used must prepare respectively different light source apparatus copending on the kinds of the scopes and must make different operations. Thus, the economy and efficiency have been low.

By the way, a system wherein a fiber scope provided with an optical fiber bundle for transmitting images is connected to a controlling apparatus for an electronic scope provided with a frame sequential type light source apparatus so that the image may be observed on such displaying picture surface as a monitor television is disclosed in the gazette of a Japanese patent application laid open No. 243625/1985. However, with this system, no electronic scope of a color mosaic type can be used and no naked eye observation can be made by using a fiber scope.

OBJECT AND SUMMARY OF THE INVENTION

An object of the present invention is to provide an endoscope light source apparatus which can feed an illuminating light adapted to a scope provided with a frame sequential type imaging means, a scope provided with a color mosaic type imaging means and a fiber scope enabling a naked eye observation.

In the present invention, a filter of a frame sequential system transmitting sequentially respective color lights is interposed between a light source lamp emitting a white color light as an illuminating light and the entrance end surface of a light guide feeding the illuminating light to a scope. The illuminating light passing through this filter will be bent in the light path by a reflecting member. This bent light path will enter the entrance end surface of the light guide without passing through the filter.

The other features and advantages of the present invention will become apparent enough with the following explanation.

BRIEF DESCRIPTION OF THE DRAWINGS

FIGS. 1 to 11 relate to the first embodiment.

FIG. 1 is an explanatory view showing the formation of a light source connecting apparatus as a frame sequential illuminating light is emitted.

FIG. 2 is an explanatory view showing the formation of the light source connecting apparatus as a white color illuminating light is emitted.

FIG. 3 is a block diagram showing the apparatus formation of an endoscope apparatus.

FIG. 4 is an explanatory view showing the formation of a color mosaic type electronic scope.

FIG. 5 is an explanatory view showing the formation of a fiber scope fitted with a externally fitted field sequential type camera.

FIG. 6 is an explanatory view showing the formation of a fiber scope fitted with an externally fitted mosaic type camera.

FIG. 7 is an explanatory view showing the formation of a fiber scope.

FIG. 8 is a perspective view showing the entire system of an endoscope apparatus.

FIG. 9 is a block diagram showing the formation of a field sequential type signal processing circuit.

FIG. 10 is a block diagram showing the formation of a mosaic type signal processing circuit.

FIG. 11 is an explanatory view showing the formation of an output circuit.

FIG. 12 is a perspective view showing a connector and connector receptacle.

FIG. 13 is an explanatory view showing the formation of a light source connecting apparatus.

FIGS. 14 and 15 relate to the third embodiment of the present invention.

FIG. 15 is a block diagram showing the apparatus formation of an endoscope apparatus.

FIG. 16 relates to the fourth embodiment of the present invention.

DETAILED DESCRIPTION OF PREFERRED EMBODIMENTS

Embodiments of the present invention shall be explained in the following with reference to the drawings.

FIGS. 1 to 11 show the first embodiment of the present invention.

Figure 8:
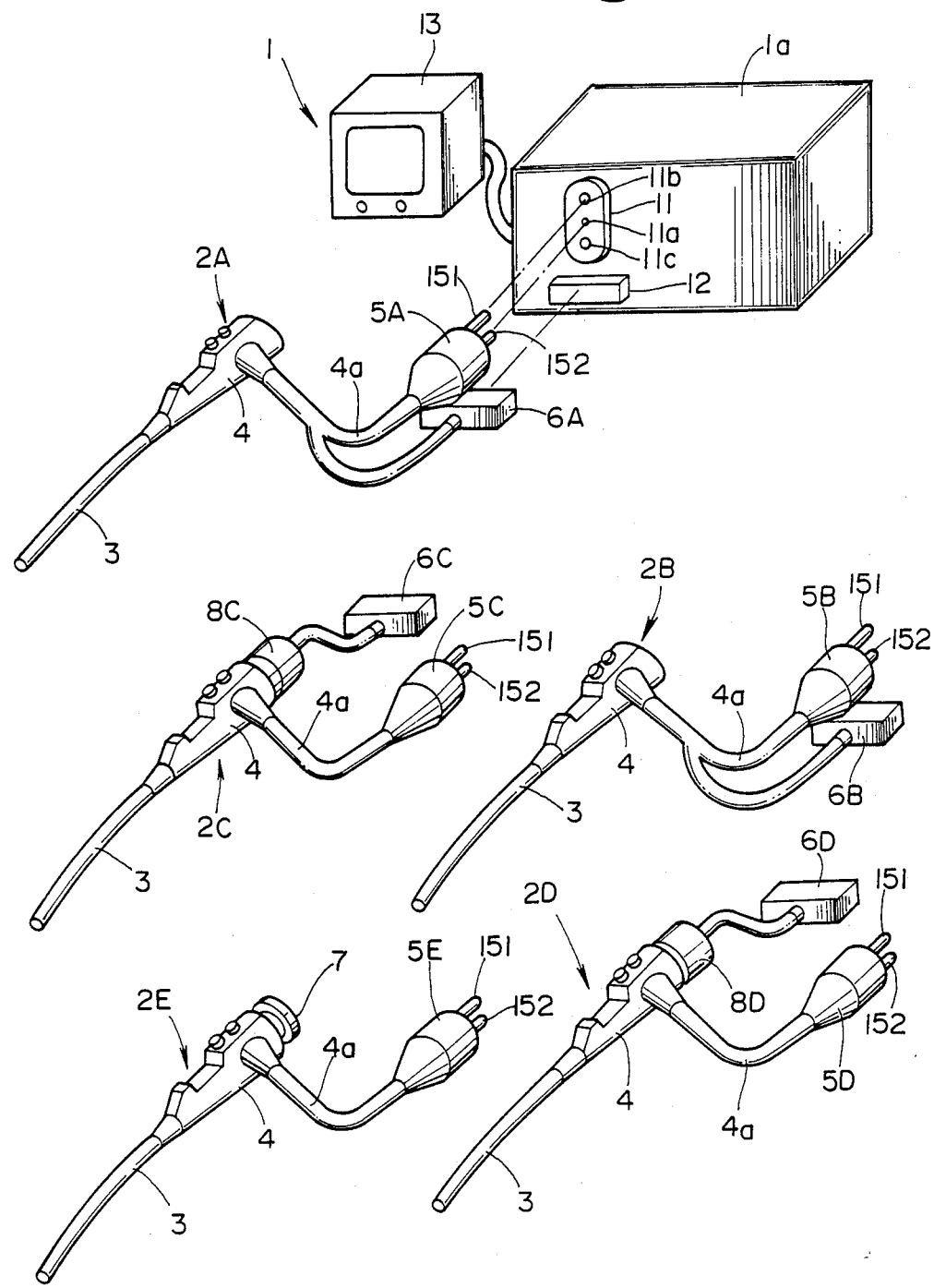

As shown in FIG. 8, an endoscope apparatus 1 is provided with a control apparatus 1a in which a light source apparatus and a video processor processing video signals are contained and to which any of various scopes (endoscopes) 2A, 2B, 2C, 2D and 2E can be connected. There are five kinds of scopes as shown in the drawing, namely, a frame sequential type electronic scope 2A, a color mosaic type electronic scope 2B using a color mosaic filter, a fiber scope externally fitted with a frame sequential type television camera (which shall be mentioned as a fiber scope fitted with a field sequential type television camera hereinafter) 2C, a fiber scope externally fitted with a color mosaic type television camera (which shall be mentioned as a fiber scope fitted with a color mosaic type television camera hereinafter) 2D and a fiber scope 2E.

The above mentioned respective scopes 2A, 2B, 2C, 2D and 2E have respectively elongate insertable parts 3 and operating parts 4 provided on the rear end of the insertable parts 3. Universal cords 4a are extended from the operating parts 4. Light source connectors 5A, 5B, 5C, 5D and 5E are provided at the tips of the universal cords 4a. By the way, the above mentioned light source connectors 5A, 5B, 5C, 5D and 5E are provided respectively with light guide connectors 151 and air and water feeding connectors 152. In the frame sequential type electronic scope 2A and color mosaic type electronic scope 2B, the above mentioned universal cords 4a are branched on the tip sides and are provided with connectors 6A and 6B at the branched tips. The fiber scope 2C fitted with the frame sequential type television camera and fiber scope 2d fitted with the color mosaic type television camera are fitted respectively with a frame sequential type television camera 8C and a color mosaic type television camera 8D and are provided respectively with signal connectors 6C and 6D at the tips of signal cables extended out of the respective television cameras 8C and 8D.

A set of connector receptacles is provided, for example, on the front surface of the housing of the control apparatus 1a so that connectors 5A, 6A; 5B, 6B; 5C, 6C; 5D, 6D; and 5E of the above mentioned respective scopes 2A, 2B, 2C, 2D and 2E (the reference numeral common to all these scopes shall be represented by 2) may be connected to the connector receptacles and the respective scopes 2 may be set to be usable. These connector receptacles are a light source connector receptacle 11 and signal connector receptacle 12. The above mentioned light source connector receptacle 11 is provided with an air and water feeding connector receptacle 11a, a frame sequential light guide connector receptacle 11b provided above this air and water feeding connector receptacle 11a and a white color light light guide connector receptacle 11c provided below the above mentioned air and water feeding connector receptacle 11a.

Figure 1:
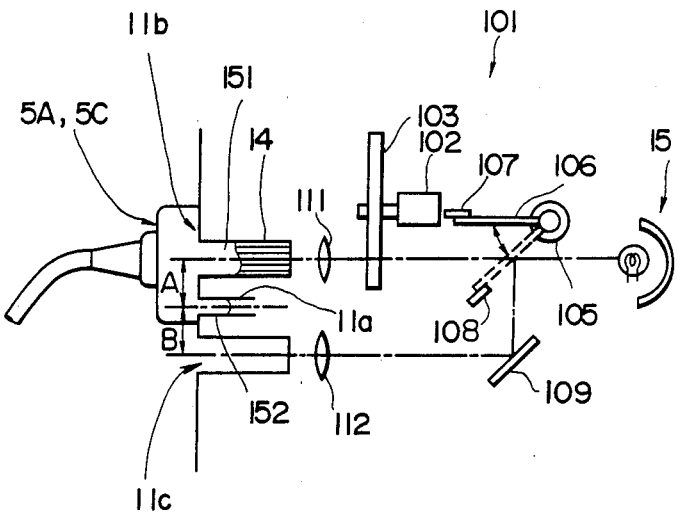

By the way, in this embodiment, as shown in FIG. 1, the distance a from the air and water feeding connector receptacle 11a to the frame sequential light guide connector receptacle 11b and the distance b from the air and water feeding connector receptacle 11a to the white color light light guide connector receptacle are made equal to each other so that the light source connectors 5A, 5B, 5C, 5D and 5E of the respective scopes 2 may be formed to be of the same shape.

As shown in FIG. 1, the respective light source connectors 5A and 5C of the same shape of the frame sequential type electronic scope 2a and the fiber scope 2C fitted with the frame sequential type television camera (these two scopes 2A and 2C shall be mentioned also a frame sequential type scopes) are so made that the light guide connector 151 may be connected to the frame sequential light guide connector receptacle 11b and the air and water feeding connector 152 may be connected to the air and water feeding connector receptacle 11a.

Figure 2:
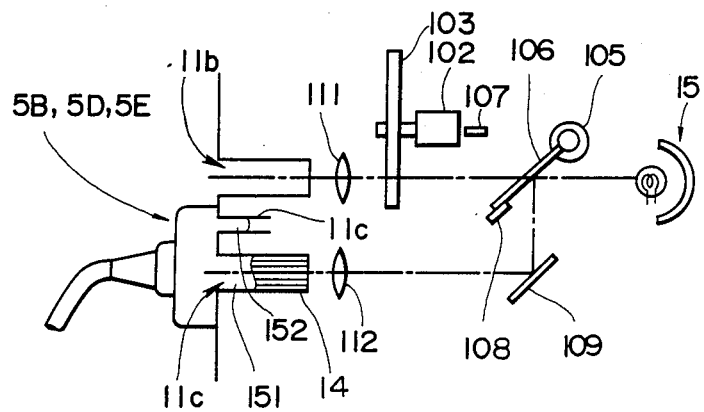
Figure 5:
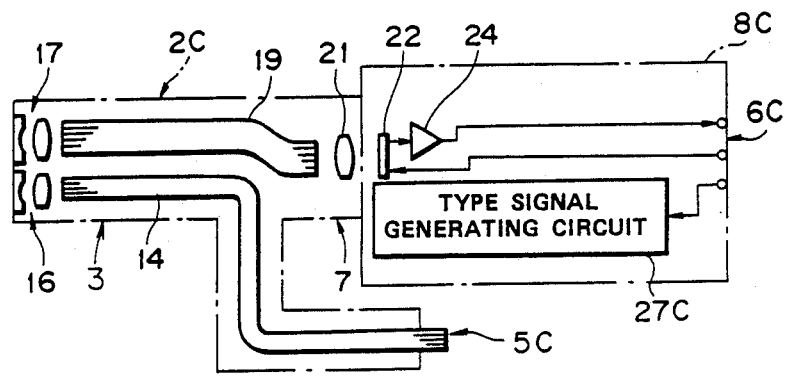
Figure 6:
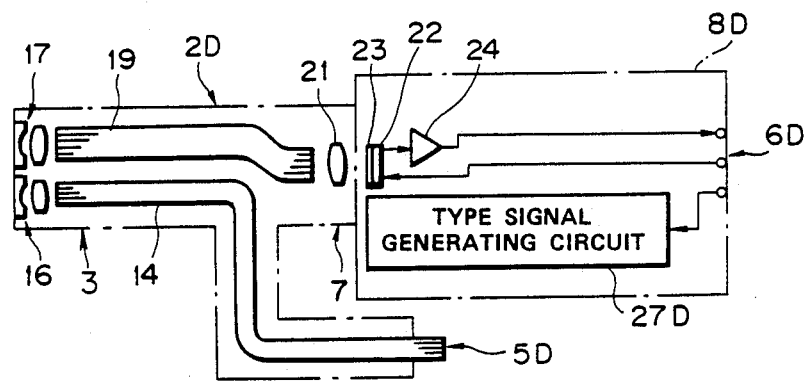
Figure 7:
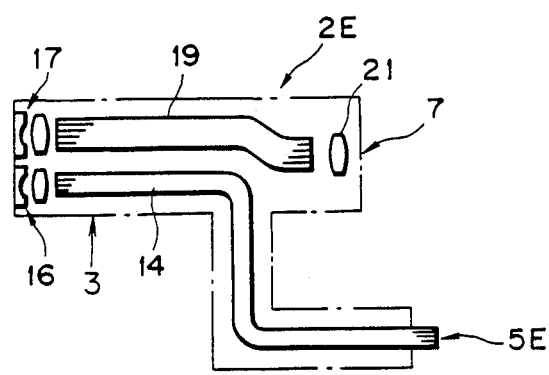

On the other hand, as shown in FIG. 2, the light source connectors 5B, 5D and 5E of the same shape of the color mosaic type electronic scope 2B, the fiber scope 2D fitted with the color mosaic type television camera(these two scopes 2B and 2D shall be mentioned also as mosaic type scopes) and the fiber scope 2E are so made that the light guide connector 151 may be connected to the white color light light guide connector receptacle 11c and the air and water feeding connector 152 may be connected to the air and water feeding connector receptacle 11a.

The above mentioned signal connector receptacle 12 adjacently below the light source connector receptacle 11 is of such shape as can connect the signal connector 6A, 6B, 6C and 6D of the same shape of the above mentioned respective scopes 2.

In case the above mentioned fiber scope 2E is connected and used, a naked eye observation will be made. However, in case the other scopes 2A, 2B, 2C and 2D are used, the displayed image will be able to be color-displayed by a color monitor 13 connected to the signal output end of the control apparatus 1a.

The interiors of the above mentioned respective scopes 2A, 2B, 2C, 2D and 2E are formed as shown respectively in FIGS. 3, 4, 5, 6 and 7.

The light guide 14 transmitting the illuminating loight is inserted through each scope 2, transmits to the exit end the illuminating light fed to the entrance end surface through a light source connecting apparatus 101 of this example from a light source 15 within the control apparatus 1a and can illuminate the front object side through a light distributing lens 16 arranged in front of this exit end surface.

In each of the above mentioned respective scopes 2, an image forming objective lens 16 is arranged in the tip part of the insertable part 3. In the frame sequential type or color mosaic type electronic endoscope 2A or 2B, such solid state imaging device 18 as a CCD is arranged in the image forming position of this objective lens 17. On the other hand, in the fiber scope 2E or the fiber scope 2C or 2D fitted with the television camera 8C or 8D, the entrance end surface of the image guide 19 is arranged to be present in the image forming position. An eyepiece lens 21 is arranged opposite to the exit end surface of the above mentioned image guide 19. In the fiber scope 2E, an observation can be made with a naked eye close to the eyepiece part 7.

On the other hand, in the fiber scope 2E fitted with the frame sequential type television camera 8C or color mosaic type television camera 8D in the eyepiece part 7, a solid state imaging device 22 is arranged through an image forming lens not illustrated opposite to an eyepiece lens 21.

An optical image formed on the imaging surface will be photoelectrically converted by the solid state imaging device 18 or 22 forming an imaging means, will be amplified by a preamplifier 24, will be transmitted to the signal connector 6 (representing 6A, 6B, 6C or 6D) side through a signal transmitting line and will be input into a video processor 25a or 25b through the signal connector receptacle 12 connected with this connector 6. A solid state imaging device driving clock signal is to be applied from a driver 26a or 26b of the above mentioned video processor 25a or 25b to the solid state imaging device 18 or 22.

The other scopes than the fiber scope 2E are provided with type signal generating circuits 27A, 27B, 27C and 27D outputting scope discriminating type signals so as to be discriminated by a discriminating circuit 28 within the control apparatus 1a.

Now, as shown in FIG. 3, the above mentioned light source 15, light source connecting apparatus 101 and two sets of video processors 25a and 25b are contained within the control apparatus 1a connectable with any of the above mentioned scopes 2.

The above mentioned light source 15 has become a white color light source emitting a white color light.

The above mentioned light source connecting apparatus 101 is formed as shown in FIGS. 1 and 2. That is to say, a rotary filter 103 having color transmitting filters of three primary colors of red (R), green (G) and blue (B) and rotated and driven by a motor 102 is provided on a light path forward of the above mentioned light source 15. A rotary mirror 106 as a light path switching means which can be interposed in and retreated from the light path of the above mentioned light source 15 by being rotated by a motor 105 is arranged between the above mentioned light source 15 and rotary filter 103. By the way, stoppers 107, 108 determining the positions of the above mentioned rotary mirror 16 as interposed and as retreated are provided at both ends of the rotating range of the above mentioned rotary mirror 106. As shown in FIG. 1, when the above mentioned rotary mirror 106 has retreated from the light path of the light source 15, the white color light emitted from the above mentioned light source 15 will pass through the above mentioned rotary filter 103. On the other hand, as shown in FIG. 2, when the above mentioned rotary mirror 106 is interposed in the light path of the light source 15, the white color light emitted from the above mentioned light source 15 will be reflected substantially in the vertical direction by the above mentioned rotary mirror 106 so as not to pass through the above mentioned rotary filter 103. A fixed mirror 109 is arranged on the light path of the light reflected by the above mentioned rotary mirror 106. The light reflected by the above mentioned rotary mirror 106 will be reflected by this fixed mirror 109 in the direction substantially parallel with the light path passing through the above mentioned rotary filter 103.

A condenser lens 111 is arranged on the light path forward of the above mentioned rotary filter 103. The above mentioned frame sequential light guide connector receptacle 11 is arranged on the light path forward of this condenser lens 111. The frame sequential illuminating light having passed through the above mentioned rotary filter 103 and having been made lights of respective wavelengths of R, G and B sequentially will be condensed by the above mentioned condenser lens 111 and will enter the entrance end surface of the light guide connector 151 (light guide 14) of the frame sequential type scope 2A or 2C connected to the above mentioned frame sequential light guide connector receptacle 11b.

On the other hand, a condenser lens 112 is arranged on the light path forward of the above mentioned fixed mirror 109 and the above mentioned white color light light guide connector receptacle 11c is arranged on the light path forward of this condenser lens 112. The white color illuminating light having avoided the above mentioned rotary filter 103 will be condensed by the above mentioned condenser lens 112 and will enter the entrance end surface of the light guide connector 151 (light guide 14) of the mosaic type scope 2B or 2D or the fiber scope 2E connected to the above mentioned white color light light guide connector receptacle 11c.

As shown in FIG. 3, the motor 105 rotating the above mentioned rotary mirror 106 is controlled in rotation by the driving controlling circuit 115. By the above mentioned driving controlling circuit 115, a discriminating signal from the discriminating circuit 28 will be input and the motor will be driven so that the above mentioned rotary mirror 106 may be retreated from the light path of the light source 15 in case the frame sequential type scope 2A or 2C is connected and so that the above mentioned rotary mirror 106 may be interposed in the light path of the light source 15 in the other case, that is, in case the mosaic type scope 2B or 2D or the fiber scope 2E is connected or in case no scope is connected.

Now, the video processor 25a is for processing frame sequential type signals. The signal input in the signal inputting terminal of the frame sequential type signal connector receptacle 12 will be input into the frame sequential type process circuit 41a and will output signals imaged respectively under the illuminating light of the respective wavelengths of R, G and B as color signals R, G and B. These respective color signals R, G and B will be output as three primary color signals RGB from three primary color output ends 43 by an output circuit 80. The above mentioned color signals R, G and B will be converted to a composite video signal of an NTSC system and will be output from the NTSC output end 46.

By the way, a rotating position sensor 51 detecting the rotating position is provided in one place on the outer periphery of the rotary filter 103 of the above mentioned light source connecting apparatus 101. By the output of this rotating position sensor 51, the timing of the clock of the timing generator 52 will be synchronized with the rotation of the rotary filter 103 and the output of this timing generator 52 will control the timing of the frame sequential type signal processing circuit 41a.

Figure 9:
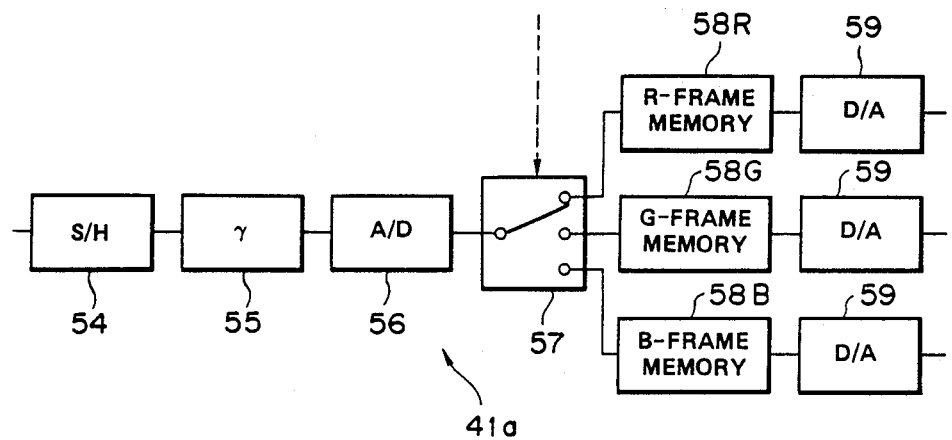

The above mentioned frame sequential type signal processing circuit 41a is formed as shown for example, in FIG. 9.

That is to say, a signal input through a preamplifier will be input in a sample holding circuit 54, will be sampleheld, will be then corrected in gamma correcting circuit 55 and will be converted to a digital signal by an A/D converter 56. The signal imaged under the frame sequence illuminations of R, G and B through a multiplexer 57 switched by the signal of the above mentioned timing generator 52 will be written into an R frame memory 58R, B frame memory 58B. The signal data written into these respective frame memories 58R, 58G and 58B will be read out simultaneously, will be converted respectively to analogue color signals R, G and B by a D/A converter 59 and will be output in an output circuit 80.

On the other hand, the signal imaged by the solid state imaging device 18 or 22 of the color mosaic type electronic scope 2B or the fiber scope 2E externally fitted with the mosaic type camera will be input into a color mosaic type process circuit 41b and a luminance signal Y and color difference signals R−Y and B−Y will be output. This signal will be input in the output circuit 80, will be converted to a composite video signal of an NTSC system and will be output from on NTSC output end 46. The above mentioned luminance signal Y and color difference signals R−Y and B−Y will be converted to color signals R, G and B by the above mentioned output circuit 80 and three primary color signals RGB will be output from three primary color signal output ends 43.

Figure 10:
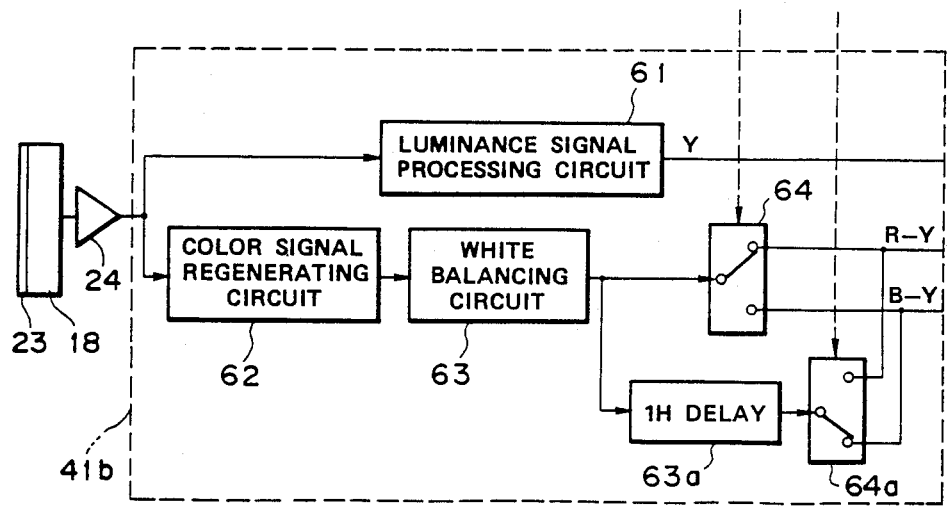

By the way, the above mentioned color mosaic type process circuit 41b is formed as shown, for example, in FIG. 10.

That is to say, the signal from the solid state imaging device 18 or 22 as amplified by the preamplifier 24 will pass through a luminance signal processing circuit 61 to produce a luminance signal Y. Also, it will be input in a color signal regenerating circuit 62 and color difference signals R−Y and B−Y will be produced in each horizontal line in time series and will be white balance—compensated by a white balancing circuit 63. One side of them will be input directly into an analogue switch 64. The other side will be delayed by one horizontal line by a 1H delaying line 63a and will be input in an analogue switch 64a and the color difference signals R−Y and B−Y will be obtained by a switching signal of the timing generator 52.

By the way, the timing generator 52 is controlled to apply signals respectively to the drivers 26a and 26b and an NTSC encoder not illustrated and to make a signal process synchronized with the driving pulse used to read signals out of the solid state imaging device 18 or 22. In this case, in the frame sequential type video processor 25a, the above mentioned timing generator 52 is synchronized with the rotary filter 103 by the output of the position sensor 51.

Now, the type signal generating circuits 27A, 27B, 27C and 27D are formed by connecting resistances or the like of respectively different resistance values, for example, between two terminals. On the other hand, the discriminating circuit 28 is enabled to discriminate the resistance value between two terminals of the connected scope by using a comparator or the like.

The above mentioned discriminating circuit 28 controls not only both drivers 26a and 26b but also the switching of the switch 113. For example, when the frame sequential type scope 2A or 2C is connected, it will be switched to the frame sequential side, the driving pulse of the driver 26a will be applied to the solid state imaging device 18 through the connector and the signal read out of the solid state imaging device 18 will be input into the frame sequential type signal processing circuit 41a.

On the other hand, when the frame sequential scope 2A or 2C is not connected a the mosaic type signal processing circuit side will be selected. By thus forming the circuit, it can be used also as a light source for the fiber scope. By the way, the switch 113 may be switched to the mosaic type side by detecting the case of the mosaic type scope 2B or 2D.

The above mentioned discriminating circuit 28 can cope with either system by feeding the control signal also to the timing generator 52.

Figure 11:
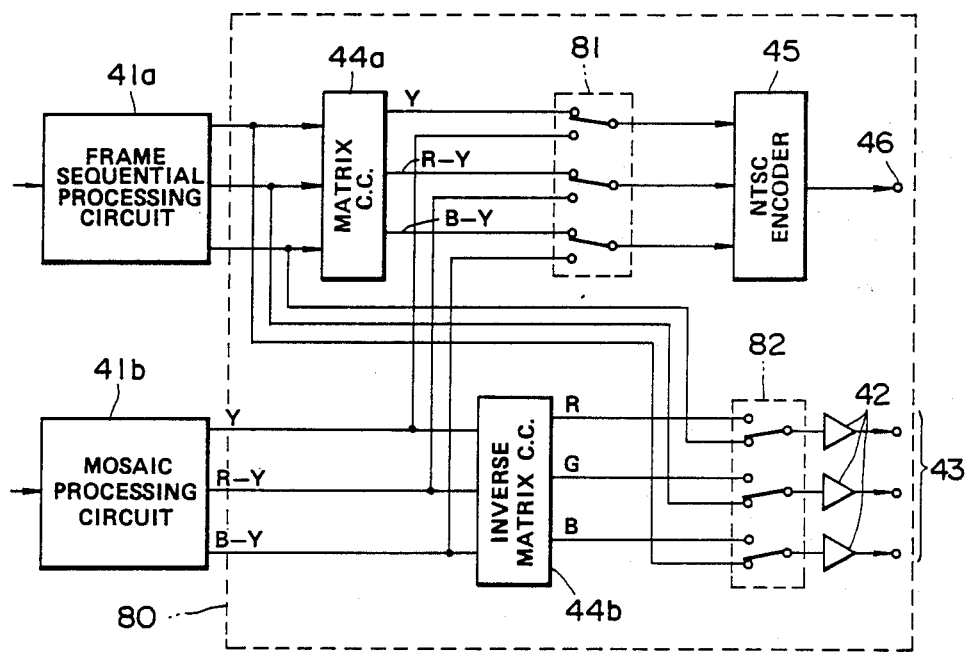

As shown in FIG. 11, the output circuit 80 is provided with switch 81 of three circuits and two contacts between the output end of a matrix circuit 44a and an NTSC encoder 45 and with switch 82 of three circuits and two contacts between the output end of an inverse matrix circuit 44b and buffers 42 forming a driver.

In the above mentioned switch 81, when one contact side is switched on, the signals of the matrix circuit 44a will be led to the common NTSC encoder 45, will be made a video signal of the NTSC system by this NTSC encoder 45 and will be output from a common NTSC output end 46 and, when the other contact side is selected, the signals of the mosaic type process circuit 41b will be led to the NTSC encoder 45 and will be output from the common NTSC output end 46.

On the other hand, on the other switch 82, when the frame sequential side is selected, the output signal of the frame sequential type process circuit 41a will pass through the common buffers 42 forming the driver and three primary color signals will be output from a common RGB output and 43. When the mosaic type signal processing circuit side is selected, three primary color signals R, G and B will be output from the common RGB output end 43 through the inverse matrix circuit 44b.

The above mentioned switches 81 and 82 can be switched manually or as operatively connected.

Thus, in this embodiment, the light source 15 common to all the scopes 2 is provided within the control apparatus 1a and the frame sequential type scopes 2A and 2C, mosaic type scope 2B and 2D and fiber scope 2E can be connected to the same light source 15 through the light source connecting apparatus 101. That is to say, when the frame sequential type scope 2A or 2C is connected to the control apparatus 1a, the rotary mirror 106 will be retreated from the light path by the discriminating signal from the discriminating circuit 28 and the white color light emitted from the light source 15 will pass through the rotary filter 103, will be made lights of the respective wavelengths of R, G and B sequentially and will be fed to the light guide connector 151 (light guide 14) of the above mentioned frame sequential type scope 2A or 2C connected to the frame sequential light guide connector receptacle 11b. On the other hand, when the mosaic type scope 2B or 2D or fiber scope 2E is connected to the control apparatus 1a, the rotary mirror 106 will be interposed in the light path of the light source 15, the white color light emitted from the light source 15 will be reflected by the above mentioned rotary mirror 106, will avoid the above mentioned rotary filter 103 and will be fed to the light guide connector 151 (light guide 14) of the above mentioned mosaic type scopes 2B or 2D or fiber scope 2E connected to the white color light light guide connector receptacle 11c.

By the way, in this embodiment, the distance from the air and water feeding connector receptacle 11a to the frame sequential light guide connector receptacle 11b and the distance from the air and water feeding connector receptacle 11a to the white color light light guide connector receptacle 11c may be made different from each other and the shape of the light source connector 5A or 5C of the frame sequential type scope 2A or 2C and the shape of the light source connector 5B, 5D or 5E of the mosaic type scope 2B or 2D or fiber scope 2E may be made correspondingly different from each other so that the mis-connection to the connector receptacle of another system may be thereby prevented.

Figure 12:
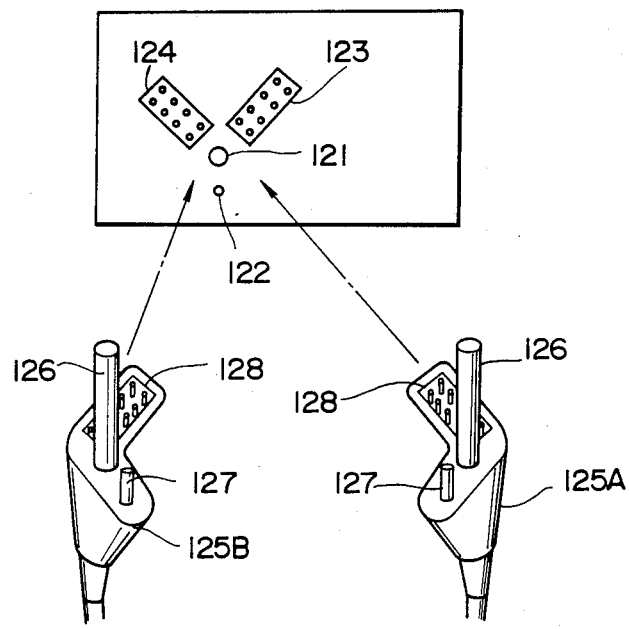
FIGS. 12 and 13 relate to the second embodiment of the present invention.
Figure 13:
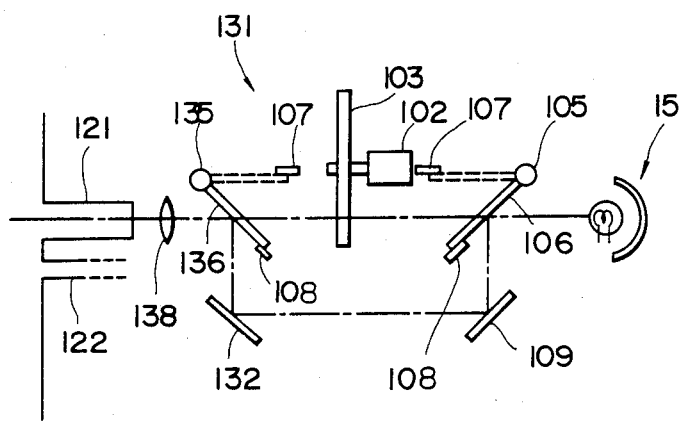

FIGS. 12 and 13 show the second embodiment of the present invention.

In this embodiment, as shown in FIG. 12, on the front surface, for example, of the housing of the control apparatus 1a, a light guide connector receptacle 121 and air and water feeding connector receptacle 122 common to all the scope 2 are provided adjacently above and below, for example, a frame sequential type signal connector receptacle 123 is provided on the upper right side of the above mentioned light guide connector receptacle 121 and a mosaic type signal connector receptacle 124 is provided on the upper left side of the above mentioned light guide connector receptacle 121. That is to say, the air and water feeding connector receptacle 122, frame sequential type signal connector receptacle 123 and mosaic type signal connector receptacle 124 are radially arranged at substantially equal angles with the light guide connector receptacle 121 in the center.

Also, in this embodiment, the frame sequential type electronic scope 2A and color mosaic type electronic scope 2B are provided respectively with a frame sequential type connector 125A and mosaic type connector 125B in each of which the light source connector and signal connector are made integral. Each of the above mentioned connected 125A and 125B is provided with the light guide connector 126, air and water feeding connector 127 and signal connector 128. Between both connectors 125a and 125B, the positions of the signal connectors 128 with respect to the light guide connectors 126 and air and water feeding connectors 127 are symmetrical to each other on the right and left correspondingly to the positions of the above mentioned frame sequential type signal connector receptacle 123 and mosaic type signal connector receptacle 124. When the light guide connector 126 and air and water feeding connector 127 are connected respectively to the light guide connector receptacle 121 and air and water feeding connector receptacle 122, the signal connector 128 of the frame sequential type connector 125A will be connected only to the frame sequential type signal connector receptacle 123 and the signal connector 128 of the mosaic type connector 125B will be connected only to the mosaic type signal connector receptacle 124.

As shown in FIG. 13, in the light source connecting apparatus 131, a fixed mirror 132 is further arranged on the light path forward of the fixed mirror 109 in the first embodiment. The light reflected by the above mentioned fixed mirror 109 will be reflected by this fixed mirror 132 substantially vertically to the light path side passing through the rotary filter 103. A rotary mirror 136 can be interposed in front of or remove from the front of the above mentioned rotary filter 103 by being rotated by a motor 135. The mirror 136 is arranged in the position in which the light path of the light having passed through the above mentioned rotary filter 103 and the light path of the light reflected by the above mentioned fixed mirror 132 intersect each other. Stoppers 107 and 108 determining the positions when the above mentioned rotary mirror 136 is interposed and retreated are provided at both ends of the rotating range of this rotary mirror. The above mentioned rotary mirror 136 will be rotated as operatively connected with the rotary mirror 106. As shown by solid lines in FIG. 13, in case the rotary mirror 106 in interposed in the light path of the light source 15, the rotary mirror 136 will be interposed in front of the rotary filter 103, the white color light emitted from the light source 15 will be reflected by the rotary mirror 106, fixed mirror 109, fixed mirror 132 and rotary mirror 136, will avoid the rotary filter 103, will be condensed by the condenser lens 138 and will reach the light guide connector 121. On the other hand, as shown by the broken lines in FIG. 13, in case the rotary mirror 106 is retreated from the light path of the light source 15, the rotary mirror 136 will be retreated from the front of the rotary filter 103, the white color light emitted from the light source 15 will pass through the rotary filter 103 and will reach the above mentioned light guide connector receptacle 121 as a frame sequential illuminating light.

By the way, the light source connectors 5B, 5D and 5E of the fiber scope 2C fitted with the frame sequential type television camera, fiber scope 2D fitted with the color mosaic type television camera and fiber scope 2E can be also connected to the above mentioned light guide connector receptacle 121 and air and water feeding connector receptacle 122. Also, the signal connector 6C of the fiber scope 2C fitted with the frame sequential type television camera can be connected to the above mentioned frame sequential type signal receptacle 123 and the signal connector 6D of the fiber scope 2D fitted with the color mosaic type television camera can be connected to the mosaic type signal connector receptacle 124.

Thus, according to this embodiment, the frame sequential type scopes 2A and 2C, mosaic type scopes 2B and 2D and fiber scope 2E can be connected to the same light source 15 through the light source connecting apparatus 131 and the light guide connectors 126 of all the scopes 2 can be connected to the common light guide connector receptacle 121.

Further, the signal connector 128 of the frame sequential type electronic scope 2A is connected only to the frame sequential type signal connector receptacle 123 and the signal connector 128 of the mosaic type electronic scope 2B is connected only to the mosaic type signal connector receptacle 124. Therefore, the connection between both scopes 2A and 2B is prevented.

By the way, the shapes of the connectors and connector receptacles are not limited to those shown in FIGS. 1 and 2. For example, the signal connector receptacles 123 and 124 may be provided on the left and right sides of the right guide connector receptacle 121.

The light source connecting apparatus is not limited to being contained integrally with the light source 15a within the control apparatus 1a but may be formed as a unit and may be connected to the exit side of any white color light source so that scopes different in the imaging system and such scope with which a naked eye observation is possible as a fiber scope may be connected to the same light source.

The other formations, operations and effects are the same as in the first embodiment.

Figure 14A:
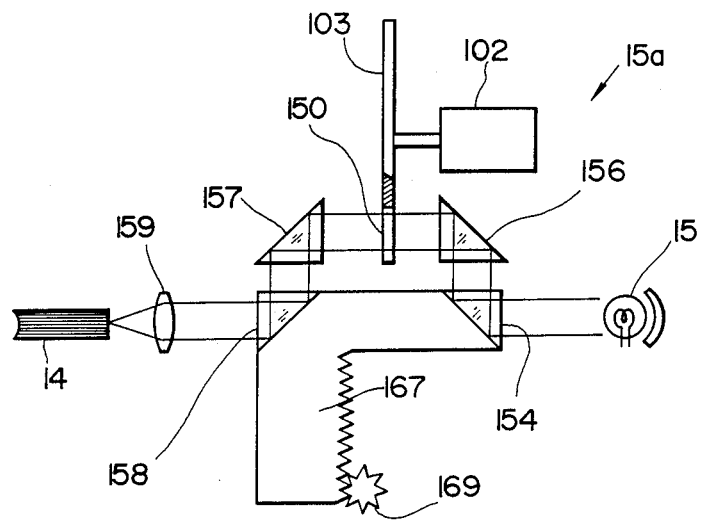
FIG. 14(a) is a formation explaining view of a light source apparatus when R, G and B color lights are emitted.
Figure 14B:
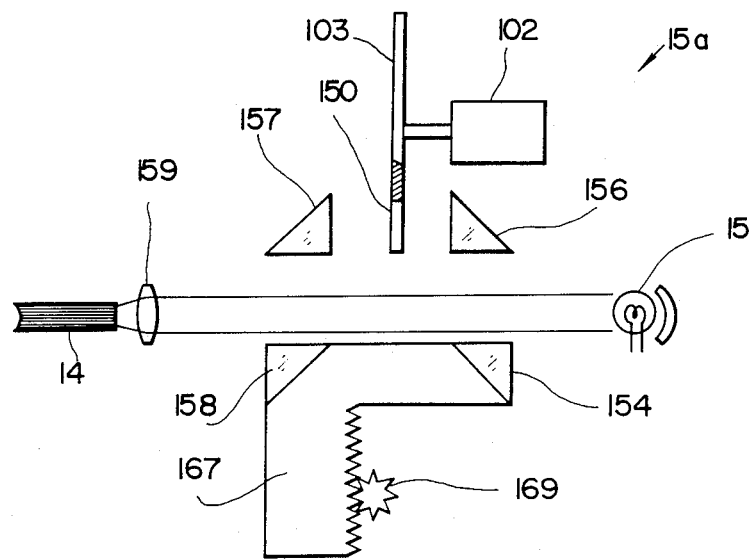
FIG. 14(b) is a formation explaining view of the light source apparatus when a white color light is emitted.
Figure 15:
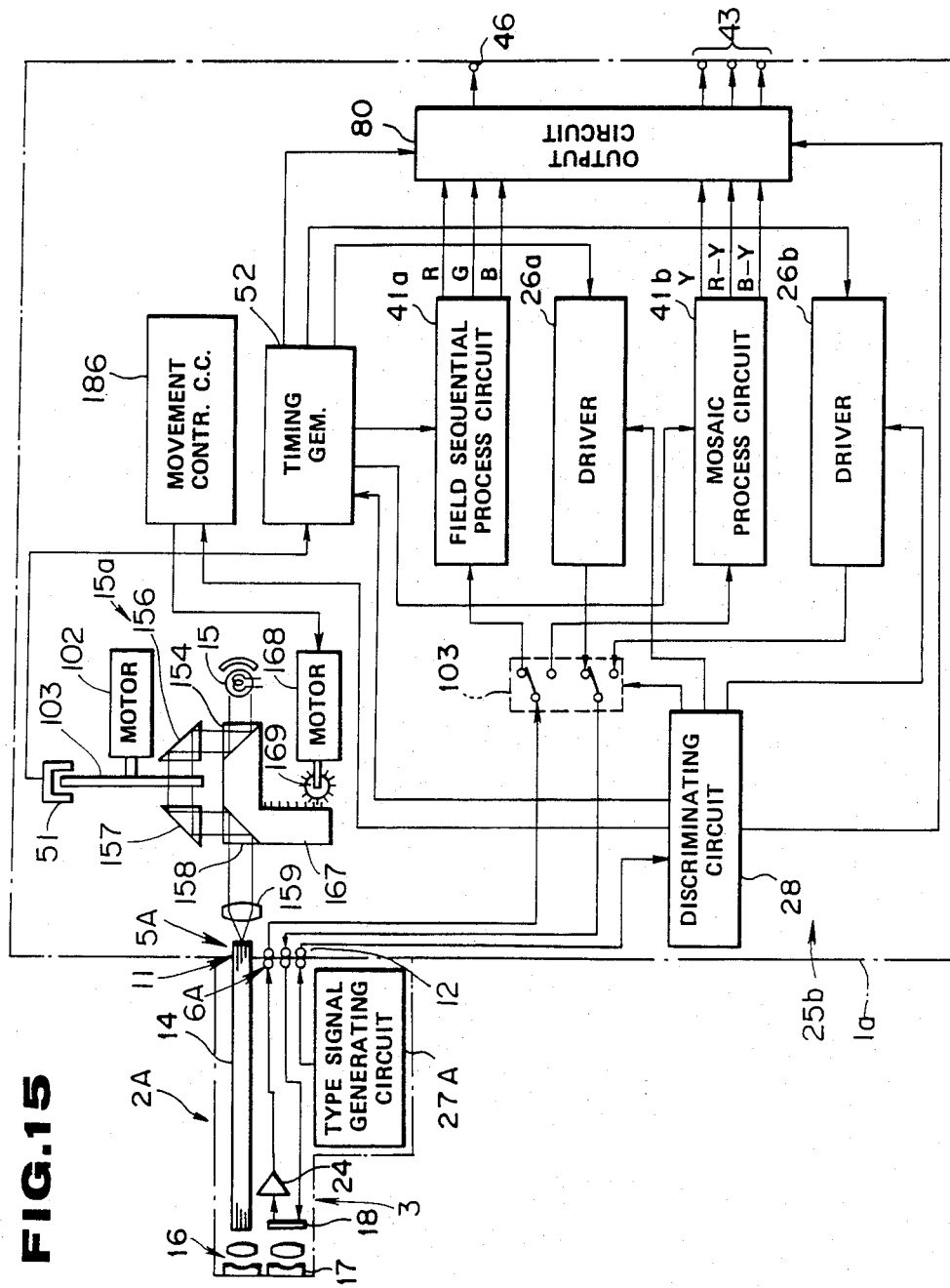

FIGS. 14 and 15 show the third embodiment of the present invention.

A light source part 15a of this embodiment is formed as in FIGS. 14(a) and 14(b). A first total internal reflection prism 154 and fourth total internal reflection prism 158 are provided on an optical axis connecting the entrance end surface of a light guide 14 with a light source 15 and the reflecting directions are provided so as to be at right angles with the above mentioned optical axis and to be able to reflect respectively in the parallel direction.

In the reflecting direction of the above mentioned first total internal reflection prism 154, a second total internal reflection prism 156 is provided so that the reflecting direction of the second total internal reflection prism 156 may be in the same direction as of the optical axis connecting the light source 15 and light guide 14.

In the reflecting direction of the above mentioned fourth total internal reflection prism 158, a third total internal reflection prism 157 is provided so as to be able to receive the reflected light of the above mentioned second total internal-reflection prism 156, and to be able conduct to the reflected light to the fourth total internal reflection prism 158.

Further, between the above mentioned second total internal reflection prism 156 and third total internal reflection prism 157, filters 150 transmitting three primary colors of red (R), green (G) and blue (B) are provided in the peripheral direction of a disc-like rotary filter 103 driven by a motor 102.

A condenser lens 159 is provided between the fourth total internal reflection prism 158 and the entrance end surface of the light guide 14.

The above mentioned first total internal reflection prism 154 and fourth total internal reflection prism 158 are held together in the upper part of a rack 167 meshed with a pinion 169 provided on a driving shaft of a moving motor 168 so as to be able to retreat from the optical axis connecting the light source 15 and the entrance end surface of the light guide 14.

Now, when the light source connectors 5a and 5C and signal connectors 6A and 6C of the frame sequential type electronic scope 2a and fiber scope 2C externally fitted with the frame sequential type camera are connected, by the signals from the type signal generating circuits 27A and 27C, the discriminating circuit 28 will judge the connected scope 2 and will instruct a movement controlling circuit 186, for example, to normally rotate the moving motor 168. Thereby, the first total internal reflection prism 154 and fourth total internal reflection prism 158 provided in the upper part of the rack 167 will be projected into the light path from the light source 15 to the condenser lens 159, the light emitted from the light source will pass through the first total internal reflection prism 154 and second total internal reflection prism 156, will be made illuminating lights of the respective wavelengths of R, G and B sequentially by the light transmitting filters 150 provided in the rotary filter 103, will be focused by the condenser lens 159 through the third total internal reflection prism 157 and fourth total internal reflection prism 158 and will be able to enter the entrance end surface of the light guide 14.

On the other hand, when the light source connectors 5B, 5D and 5E and signal connectors 6B and 6D of the color mosaic type electronic scope 2B, fiber scope 2D externally fitted with the color mosaic type camera and fiber scope 2E are connected, by the signals from the type signal circuit 27B and 27d, the discriminating circuit 28 will discriminate the connected scope 2 and will instruct the movement controlling circuit 186, for example, to reversely rotate the moving motor 168. Thereby, as shown in FIG. 14(b), the first total internal reflection prism 154 and fourth total internal reflection prism 158 will retreat from the light path connecting the light source 15 and condenser lens 154 and the white color light will be focused by the condenser lens 159 and will enter the entrance end surface of the light guide 14.

By the way the total internal reflection prism forming be changed by moving the second total internal reflection prism 156 and third total internal reflection prism 157.

The other formations, operations and effects are the same as in the first embodiment.

FIG. 16 shows the fourth embodiment of the present invention.

Figure 16A:
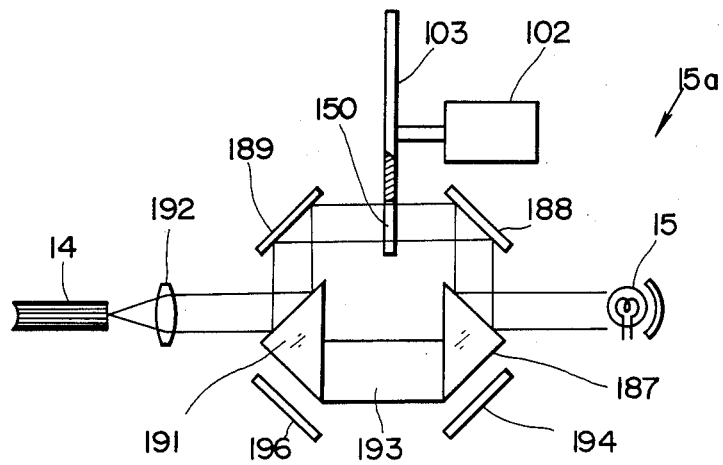
FIG. 16(a) is a formation explaining view of light source apparatus when R, G and B color lights are emitted.
Figure 16B:
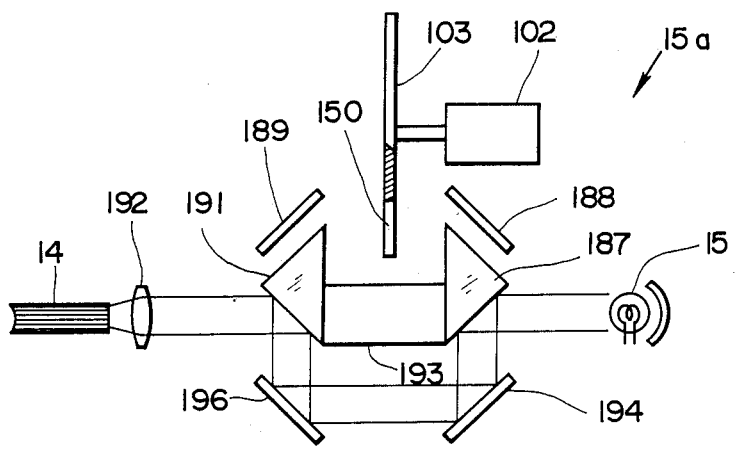
FIG. 16(b) is a formation explaining view of the light source apparatus when a white color light is emitted.

A light source part 15a of this embodiment is formed as shown in FIGS. 16(a) and 16(b).

A first total reflection prism 187 and second total reflection prism 191 are provided on the optical axis connecting a light source 15 and the entrance end surface of light guide 14.

The above mentioned first total reflection prism 187 includes the optical axis in one of the planes forming a right angle and this plane is provided to have an angle of 45 degrees with the optical axis. The second total reflection prism 191 is provided symmetrically with the diagonal side of the above mentioned first total reflection prism 187.

In the reflecting direction of the above mentioned first total reflection prism 187, a first mirror 188 is provided so as to be able to reflect an entering light in the same direction as the emitting direction of the light source 15. Also, in the reflecting direction of the second total reflection prism 191, in the same manner, a second mirror 189 is provided so as to be able to receive the reflected light of the above mentioned first mirror 188.

Between the above mentioned first mirror 188 and second mirror 189, color transmitting filters 150 provided in a rotary filter 103 are arranged so as to intercept the light path.

A third mirror 194 is provided in the reflecting direction of the other plane of the above mentioned first total reflection prism 187 so that the reflected light of the third mirror 194 may enter a fourth mirror 196 provided in the reflecting direction of the above mentioned second total reflection prism.

A condenser lens 192 is provided between the second total reflection prism 191 and the entrance end surface of the light guide 14.

The above mentioned first total reflection prism 187 and second total reflection prism 191 are held together by a holding member 193 provided with a moving means not illustrated.

Now, when the light source connectors 5A and 5C and signal connectors 6A and 6C of the frame sequential type electronic scope 2A and the fiber scope 2C externally fitted with the frame sequential type camera are connected, by the signals from the type signal generating circuits 27A and 27C, the discriminating circuit 28 will judge the connected scope 2 and will instruct the movement controlling circuit 186, for example, to normally rotate the moving motor 168. thereby, by such moving means as, for example, a rack and pinion not illustrated, as shown in FIG. 16(a), by the holding member 193, the first total reflection prism 187 and second total reflection prism 191 will be moved onto the optical axis connecting the light source 15 and the entrance and surface of the light guide 14 so that the white color light may enter one of the planes holding a right angle of the first total reflection prism 187 and may pass through the color transmitting filters 150.

On the other hand, when the light source connectors 5B, 5D and 5E and signal connectors 6B and 6D of the color mosaic type electronic scope 2B, fiber scope 2D externally fitted with the color mosaic type camera and fiber scope 2E are connected, by the signals from the type signal circuits 27B and 27D, the discriminating circuit 28 will judge the connected scope 2 and will instruct the movement controlling circuit 186, for example, to reversely rotate the moving motor 168.

Thereby, by such moving means as, for example, a rack and pinion, the holding member 193 will be moved so that the emitted light of the light source 15 may enter the third mirror 194.

The other formations and operations are the same as in the first embodiment.

By such formation as in the above mentioned respective embodiments, by providing an optical system wherein a light path reaching an object by passing through color filters and a light path reaching the object without passing through the color filters can be selected, as an illuminating light adapted to a scope provided with a frame sequential type imaging means and a white color light can be output, an illuminating light adapted to a scope provided with a frame sequential type imaging means, scope provided with a color mosaic type imaging means and fiber scope enabling a naked eye observation can be fed.

What is claimed is:

1. An endoscope light source apparatus comprising:
    a light source means for emitting a white color light as an illuminating light;
    a filter means in a light path of the illuminating light source for sequentially transmitting respective color lights adapted to a frame sequential color imaging system; and
    a light path switching means for selectively switching the light path from said light source between a light path passing through said filter means and a light path avoiding said filter means.

2. An endoscope light source apparatus according to claim 1 wherein said filter means is a rotary filter provided with color transmitting filters in the peripheral direction and a driven by a driving means.

3. An endoscope light source apparatus according to claim 1 wherein said light path switching means is formed of reflecting members.

4. An endoscope light source apparatus according to claim 1 further comprising a connecting means for connecting an entrance end of a light guide for an endoscope to said light source means whereby the illuminating light on the light path passing through said filter means and the illuminating light on the light path avoiding said filter means are made to enter the entrance end of said light guide.

5. An endoscope light source apparatus according to claim 4 where in said connecting means has a first connecting part connectable with the entrance end of the light guide of a scope provided with a frame sequential type imaging means and a second connecting part connectable with the entrance end of the light guide of a scope requiring a white color illumination.

6. An endoscope light source apparatus according to claim 4 wherein said connecting means has a connecting part selectively connectable with the entrance end of the light guide of a scope provided with a frame sequential type imaging means and with the entrance end of the light guide of a scope requiring a white color illumination.

7. An endoscope light source apparatus according to claim 1, further comprising an identifying means for identifying whether an endoscope to be connected is to be used in a frame sequential color imaging system or to be used in a system which necessitates white color light as an illuminating light and outputting an identifying signal, and operating said light path switching means based on the identifying signal.

* * * * *